United States Patent [19]

Lunder

[11] Patent Number: 5,107,000
[45] Date of Patent: Apr. 21, 1992

[54] PROCESS FOR OBTAINING CATECHIN COMPLEXES

[75] Inventor: Tito L. Lunder, Morges, Switzerland

[73] Assignee: Nestec S. A., Vevey, Switzerland

[21] Appl. No.: 687,375

[22] Filed: Apr. 18, 1991

[30] Foreign Application Priority Data

May 9, 1990 [CH] Switzerland .................. 1573/90

[51] Int. Cl.⁵ .......................................... C07D 311/62
[52] U.S. Cl. .................................................. 549/399
[58] Field of Search ........................................ 549/399

[56] References Cited

U.S. PATENT DOCUMENTS

| 4,248,789 | 2/1981 | Okada | 549/399 |
| 4,613,672 | 9/1986 | Hara | 549/399 |
| 4,673,530 | 6/1987 | Hara | 549/399 |
| 4,913,909 | 4/1990 | Hara et al. | 549/399 |

*Primary Examiner*—Nicky Chan
*Attorney, Agent, or Firm*—Vogt & O'Donnell

[57] ABSTRACT

Catechin complexes are obtained from aqueous extracts obtained from plants containing catechins. The extracts are concentrated to a liquor, and the liquor then is extracted with dichloromethane to eliminate pigments from the liquor and to obtain an aqueous phase, which contains catechin complexes, and a dichloromethane phase. The aqueous phase is mixed with purified sea sand to form a paste which is eluted with acetone to obtain the catechin complexes in the acetone. The catechin complexes are recovered from the acetone by evaporating the acetone, and the recovered catechin complexes may be dried to obtain a powder.

5 Claims, No Drawings

PROCESS FOR OBTAINING CATECHIN COMPLEXES

BACKGROUND OF THE INVENTION

This invention relates to a process for obtaining catechin complexes.

Hitherto, processes for obtaining catechin complexes from tea or other plants have involved the use of hot solvents which increased the risks of polymerization. Catechins can also be cold-extracted, although the condensed tannins have to be eliminated by saturation of the aqueous phase with sodium chloride.

SUMMARY OF THE INVENTION

The process according to the present invention enables the catechins contained in certain plants to be effectively extracted while, at the same time, eliminating the polymerized tannins.

The present invention relates to a process for obtaining catechin complexes, in which leaves of green tea or any other plant containing catechins are extracted, the extract is concentrated to the consistency of a liquor, the liquor is extracted with dichloromethane to eliminate the pigments, the aqueous phase is mixed with purified sea sand to form a paste, the catechin complexes are eluted with acetone and the acetone is evaporated. The catechin complexes recovered from the acetone may be dried to obtain a powder. The catechins are advantageously eluted with acetone containing a small quantity of water.

DETAILED DESCRIPTION OF THE INVENTION

Catechin complexes are understood in particular to be catechin, epicatechin, catechin gallate and epigallotechingallate.

Catechins are used in particular as additives in infusions of black tea in the production of instant black tea to avoid the formation of cream of tea which is a complex of caffeine and polyphenols. It is also known that catechins may be used as sources of P vitamins and may be incorporated in pharmaceutical specialities for the prevention of capillary fragility.

The red vine is another example of a plant which contains catechin complexes.

According to the invention, it has surprisingly been found that, if purified sea sand is used, the polymerized tannins are strongly retained on the sand while the catechins are readily eluted with acetone advantageously containing a small quantity of water.

The tea leaves are extracted, which may be performed by infusing the leaves, in batches in counter-current either hot at a temperature of 90° to 130° C. under a pressure of 1 to 3 bar, preferably 2 bar, over a period of 10 to 30 minutes or cold at a temperature of 20° to 30° C. under atmospheric pressure over a period of 5 to 6 hours. The cold treatment enables the product to preserve and prevents oxidation of the catechins while the hot treatment enables the extraction yield to be increased.

After extraction, the leaves are separated by centrifugation, and the extract is concentrated to a heavy liquor having a dry matter content of 25 to 30% by conventional methods.

The pigments are eliminated by liquid-liquid extraction with a solvent, such as dichloromethane. The ratio by volume of liquor to solvent in this extraction step is from 1:5 to 1:20.

The aqueous phase is then mixed with purified sea sand in a percolator, in a column or in any other apparatus which allows the subsequent evaporation of water. The catechins are eluted with acetone containing a small quantity of water. The acetone is poured onto the mixture of sea sand and tea and is recycled several times to guarantee complete elution of the catechin complexes.

The acetone is then removed under reduced pressure and drying is continued until a yellowish powder is obtained. The aqueous solution obtained after removal of the acetone may also be dried by spray-drying or freeze-drying.

The yield of the process according to the invention is of the order of 60 to 70%.

EXAMPLES

The invention is illustrated by the following Examples.

EXAMPLE 1

100 g of dry green tea leaves are infused in deionized water at 95° C. for 10 minutes.

The spent leaves are separated by centrifugation and the clear infusion is concentrated under reduced pressure to the consistency of a heavy liquor having a dry matter content of the order of 27 to 30%.

This heavy liquor is extracted with dichloromethane to remove the pigments in the green tea.

The aqueous phase is mixed with a sufficient quantity of purified sea sand to form a paste which is dried in vacuo at 70° C. The catechins are eluted with 200 ml acetone containing 5% water. The tea/sand mixture is rewashed with 100 ml acetone containing 5% water.

The organic phase is evaporated under reduced pressure and concentration of the aqueous phase is continued until a residue of syrupy consistency is obtained; this residue is spray-dried. Alternatively, after removal of the acetone, the aqueous phase may be freeze-dried. The powder thus obtained is soluble in water and ethanol.

EXAMPLE 2

100 ml of dry green tea leaves are extracted in a cell with deionized water at 130°–125° C. under a pressure of 2 bar over a period of 15 minutes during which the extract is continuously recycled.

The spent leaves are washed with fresh water which is added to the preceding extract. Centrifugation or filtration is generally not necessary because the layers of leaves and the stubs on the bottom and top of the covers act as effective filters.

The extract is evaporated to a dry matter content of approximately 20 to 25% and the residue is extracted with dichloromethane to eliminate the pigments.

The viscous aqueous phase is mixed with a sufficient quantity of purified sea sand to form a paste which is dried in vacuo at 60° C.

The catechins are retained on the sand and are then eluted with acetone containing 5% water.

The organic phase is evaporated under reduced pressure and concentration of the aqueous phase is continued until a residue of syrupy consistency is obtained; this residue is spray-dried. Alternatively, after removal of the acetone, the aqueous phase may be freeze-dried.

The powder thus obtained is soluble in water and ethanol.

I claim:

1. A process for obtaining catechin complexes comprising extracting leaves of green tea with water to obtain an aqueous extract, concentrating the aqueous extract to obtain a liquor, extracting the liquor with dichloromethane to eliminate pigments from the liquor and obtaining an aqueous phase and a dichloromethane phase, mixing the aqueous phase with purified sea sand to form a paste, eluting the paste with acetone to obtain catechin complexes in the acetone and evaporating the acetone to recover the catechin complexes from the acetone.

2. A process as claimed in claim 1 wherein the leaves of green tea are extracted at a temperature of from 90° C. to 130° C. under a pressure of from 1 bar to 3 bar over a period of 10 minutes to 30 minutes.

3. A process as claimed in claim 1 wherein the leaves of green tea are extracted at a temperature of from 20° C. to 30° C. under atmospheric pressure over a period of from 5 hours to 6 hours.

4. A process as claimed in claim 1 wherein the extract is concentrated to a dry matter content of from 25% to 30%.

5. A process as claimed in claim 1 wherein the liquor is extracted with dichloromethane in a ratio by volume of liquor to dichloromethane of from 1:5 to 1:20.

* * * * *